(12) United States Patent
Huberman

(10) Patent No.: US 9,056,099 B2
(45) Date of Patent: Jun. 16, 2015

(54) COMPOSITIONS AND METHODS FOR TREATING VIRAL DISEASES

(75) Inventor: Eliezer Huberman, Chicago, IL (US)

(73) Assignee: NovaDrug, LLC, Chicago, IL (US)

( * ) Notice: Subject to any disclaimer, the term of this patent is extended or adjusted under 35 U.S.C. 154(b) by 394 days.

(21) Appl. No.: 13/582,277

(22) PCT Filed: Feb. 25, 2011

(86) PCT No.: PCT/US2011/026174
§ 371 (c)(1),
(2), (4) Date: Nov. 16, 2012

(87) PCT Pub. No.: WO2011/109232
PCT Pub. Date: Sep. 9, 2011

(65) Prior Publication Data
US 2013/0059881 A1     Mar. 7, 2013

Related U.S. Application Data

(60) Provisional application No. 61/309,328, filed on Mar. 1, 2010.

(51) Int. Cl.
*A61K 31/44* (2006.01)
*A61K 31/437* (2006.01)

(52) U.S. Cl.
CPC .................................. *A61K 31/437* (2013.01)

(58) Field of Classification Search
CPC ... A61K 31/44; A61K 31/437; C07D 417/04; C07D 487/04; C07D 401/04; C07D 401/14; C07D 401/12; C07D 401/06
USPC .......................................... 514/300; 546/113
See application file for complete search history.

(56) References Cited

U.S. PATENT DOCUMENTS

| | | | |
|---|---|---|---|
| 5,627,165 | A | 5/1997 | Glazier |
| 2004/0254200 | A1 | 12/2004 | Davis et al. |
| 2008/0097094 | A1 | 4/2008 | Schrimpf et al. |
| 2008/0207678 | A1 | 8/2008 | Bondy et al. |
| 2009/0298810 | A1 | 12/2009 | Busch-Petersen |
| 2010/0029706 | A1 | 2/2010 | Miller et al. |

FOREIGN PATENT DOCUMENTS

| | | |
|---|---|---|
| CN | 101619064 | 1/2010 |
| WO | WO 2007/124423 | 11/2007 |
| WO | 2011/109232 | 9/2011 |
| WO | WO 2011/116287 | 9/2011 |

OTHER PUBLICATIONS

He et al (Tet. Lett., 2005, 46, 1251-1254).*
STN Compound Entry Dates.*
Ago et al., "Crystal structure of the RNA_dependent RNA polymerase of hepatitis C virus," *Structure*, 7(11): 1417-1426 (1999).
Chockalignam et al., "A cell protection screen reveals potent inhibitors of multiple stages of the hepatitis C virus life cycle," *Proc. Natl. Acad. Sci. USA*, 107(8): 3764-3769 (2010).
Wei et al., "New small molecule inhibitors of hepatitis C virus," *Bioorg. Med. Chem. Lett.*, 19(24): 6926-6930 (2009).
Int'l Search Report and Written Opinion issued in app. No. PCT/US2011/026174 (2011).
Shah et al., "Synthesis and evaluation of CCR5 antagonists containing modified 4-piperidinyl-2-phenyl-1-(phenylsulfonylamino)-butane," *Bioorganic & Med. Chem. Ltrs.*, 15(4): 977-982 (2005).
Supplementary Search Report issued in EP Application No. 11751104 (2013).
Di Bisceglie et al., "New Therapeutic Strategies for Hepatitis C," *Hepatology*, 35(1): 224 (2002).
Gordon et al., "Control of Hepatitis C: A Medicinal Chemistry Perspective," *Journal of Medicinal Chemistry*, 48(1):1-19 (2005).
Hanazaki, "Antiviral Therapy for Chronic Hepatitis B: A Review," *Current Drug Targets—Inflammation & Allergy*, 3: 63-70 (2004).
'Idéo et al., "New Therapies for the Treatment of Chronic Hepatitis C," *Curr. Pharm. Des.*, 8(11): 959-966 (2002).
Kneteman et al., "Anti-HCV Therapies in Chimeric *scid*-Alb/uPA Mice Parallel Outcomes in Human Clinical Application," *Hepatology*, 43(6): 1346-1353 (2006).
Kneteman et al., "HCV796: A Selective Nonstructural Protein 5B Polymerase Inhibitor with Potent Anti-Hepatitis C Virus Activity In Vitro, in Mice with Chimeric Human Livers, and in Humans Infected with Hepatitis C Virus," *Hepatology*, 49(3): 745-752 (2009).
Lauer et al., "Hepatitis C Virus Infection," *N. Engl. J. Med.*, 345(1): 41-52 (2001).
Mercer et al., "Hepatitis C virus replication in mice with chimeric human livers," *Nat. Med.* 7(8): 927-933 (2001).
Pathalk et al., "Enzymes and protecting group chemistry," *Curr. Opn. Chem. Biol.*, 2:112-120 (1998).
Samuel, "Antiviral Actions of Interferons," *Clin. Microbiol. Rev.*, 14(4): 778-809 (2001).
Tan et al., "Hepatitis C Therapeutics: Current Status And Emerging Strategies," *Nat. Rev. Drug Disc.*, 1:867-881 (2002).
Yu et al., "Cell-based hepatitis C virus infection fluorescence resonance energy transfer (FRET) assay for antiviral compound screening," *Curr Protoc Microbiol.*, Chapter 17:Unit 17.5 (Aug. 2010).
Yu et al., "Development of a cell-based hepatitis C virus infection fluorescent resonance energy transfer assay for high-throughput antiviral compound screening" *Antimicrob. Agents Chemother.*; 53(10): 4311-4319 (2009).

* cited by examiner

*Primary Examiner* — Jason Sims
*Assistant Examiner* — Ibrahim D Bori
(74) *Attorney, Agent, or Firm* — Barnes & Thornburg LLP; Alice O. Martin

(57) ABSTRACT

Substituted perhydro pyrrolopyridines and methods for their use in the treatment of viral diseases including hepatitis C viral infections are described herein.

20 Claims, 4 Drawing Sheets

COMPOSITIONS AND METHODS FOR TREATING VIRAL DISEASES

CROSS REFERENCE TO RELATED APPLICATIONS

This application is a U.S. nationalization under 35 U.S.C. §371 of International Application No. PCT/US2011/026174, filed Feb. 25, 2011, which claims the benefit under 35 U.S.C. §119(e) of U.S. Provisional Application Ser. No. 61/309,328, filed Mar. 1, 2010. The disclosures set forth in the referenced applications are incorporated herein by reference in their entireties, including all information as originally submitted to the United States Patent and Trademark Office.

SEQUENCE LISTING

The instant application contains a Sequence Listing which has been submitted in ASCII format via EFS-Web and is hereby incorporated by reference in its entirety. Said ASCII copy, created on Feb. 25, 2011, is named 114123_SEQ_ST25.txt and is 2,103 bytes in size.

TECHNICAL FIELD

The invention described herein pertains to substituted perhydro pyrrolopyridines and methods for their use in treating viral diseases including hepatitis C viral infections.

BACKGROUND AND SUMMARY OF THE INVENTION

Hepatitis C (HCV) belongs to the Flaviviridae family of positive-sense, single-stranded RNA viruses. The HCV genome encodes a protein having 3000 amino acid residues that is processed into both structural and nonstructural proteins. HCV infection is a significant global health issue; the World Health Organization estimates that over 170 million people carry the HCV infection, which can ultimately result in chronic hepatitis, cirrhosis, and hepatocellular carcinoma. It has been reported that these complications are responsible for about 10000-20000 deaths annually in the U.S. alone. HCV is one of the leading causes of advanced liver disease and often results in patients requiring liver transplantation. Current therapies for HCV infection rely on combinations of nonspecific antiviral medications, ribavirin, and interferon-α (IFN) (see, for example, a) K. Hanazaki, Curr. Med. Chem.: Anti-Infect. Agents 2003, 2, 103; b) G. M. Lauer, B. D. Walker, N. Engl. J. Med. 2001, 345, 41; c) G. IdNo, A. Bellobuono, Curr. Pharm. Des. 2002, 8, 959; d) A. M. Di Bisceglie, J. McHutchison, C. M. Rice, Hepatology 2002, 35, 224; e) C. E. Samuel, Clin. Microbial. Rev. 2001, 14, 778; the foregoing publication, and each additional publication cited herein, is incorporated herein by reference). Not only do such treatment regimens reportedly cause undesirable side effects such as leucopenia, thrombocytopenia, and hemolytic anemia, but it has been estimated that only about 40% of patients achieve a sustained viral response (see, for example, Gordon & Keller, J. Med. Chem. 2005, 48, 1; Tan et al., Nat. Rev. Drug Discovery 2002, 1, 867). Thus, treatments for HC represent an unmet medical need, especially treatments that are more effective and/or less toxic.

It has been discovered herein that perhydro pyrrolopyridines are active antiviral agents. In particular, it has been discovered herein that perhydro pyrrolopyridines are active against HCV infections.

In one illustrative embodiment, described herein are substituted perhydro pyrrolopyridines that are useful for the treatment of viral diseases including HCV. In another embodiment, described herein are pharmaceutical compositions comprising the substituted perhydro pyrrolopyridines that are useful for the treatment of viral diseases including HCV. Illustratively, the compositions include one or more carriers, diluents, or excipients, or a combination thereof.

In another embodiment, described herein are methods for treating viral diseases including HCV, where the methods include administering the substituted perhydro pyrrolopyridines and/or the pharmaceutical compositions including the substituted perhydro pyrrolopyridines. In another embodiment, described herein is the use of one or more of the substituted perhydro pyrrolopyridines and/or the pharmaceutical compositions including the substituted perhydro pyrrolopyridines in the manufacture of a medicament for treating a patient having a viral disease. Illustratively, the viral disease is hepatitis C.

DETAILED DESCRIPTION

Figure 1:
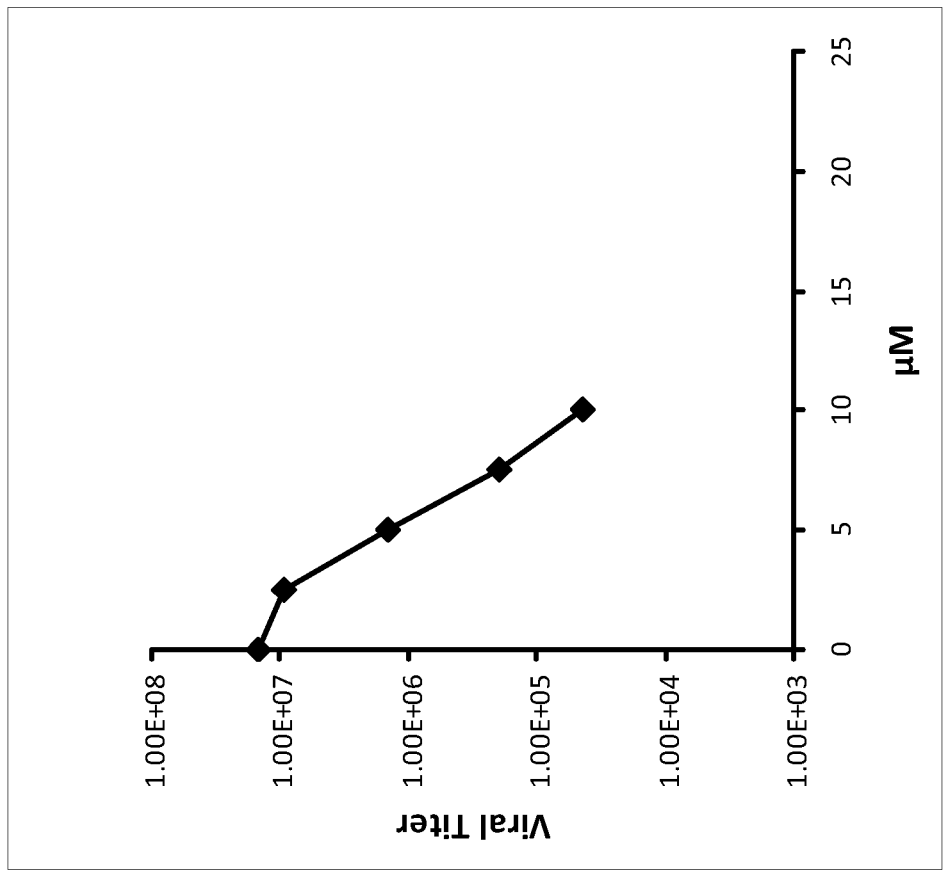
FIG. 1. Dose-response curve (μM) showing intracellular HCV RNA levels for cultures incubated with COMPOUND EXAMPLE 1: $Ar^1$=Ph, $Ar^2$=4-F—$C_6H_4$, $Ar^3$=4-MeO—$C_6H_4$.

It has been discovered herein that substituted perhydro pyrrolopyridines, including octahydro-1H-pyrrolo[3,2-c]pyridines, are useful in treating viral diseases. Without being bound by theory, it is believed herein that substituted perhydro pyrrolopyridines decrease viral load in infected cells. Illustratively, the viral diseases include hepatitis C viral infections.

It is to be understood that as used herein, the term "perhydro pyrrolopyridines", as well as the various embodiments represented by the formulae described herein, generally refers to the parent compounds as well as pharmaceutically acceptable salts thereof, including acid and/or base addition salts. In addition, it is to be understood that the term perhydro pyrrolopyridines includes various prodrugs of the compounds, as are described herein.

In one embodiment, described herein are pharmaceutical compositions comprising one or more of the substituted perhydro pyrrolopyridines. The substituted perhydropyrrolopyridines and the pharmaceutical compositions comprising them are useful in the treatment of viral infections such as HCV.

In another embodiment, described herein are methods of use of the substituted perhydropyrrolopyridines and the pharmaceutical compositions comprising them for treating viral infections. Illustratively, these methods include administering to a patient in need of relief from the viral infection a therapeutically effective amount of one or more of the substituted perhydro pyrrolopyridines and/or the pharmaceutical compositions comprising them. In one variation, the methods described herein also include co-therapies with other therapeutic agents known to be useful in treating viral infections including HCV. Accordingly, the compounds, compositions, formulations, uses, and methods described herein may be combined with any one or more of such compounds or agents known for treating viral diseases, such as HCV infections. Accordingly, in another embodiment, the co-therapy includes the co-administration of one or more of the compounds described herein and one or more of the known compounds or agents known to be useful in treating viral infections including HCV.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_6$, and $C_1$-$C_4$. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloallcylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, acylcarbonyl, and the like, each of which is optionally substituted.

As used herein, the term "carbonyl and derivatives thereof" includes the group C(O), C(S), C(NH) and substituted amino derivatives thereof.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —CO$_2$H, —NR$_2$. Illustrative prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a cotherapy.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, (21$^{st}$ ed., 2005)).

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and vehicles.

In one embodiment, described herein is a compound for treating a patient having hepatitis C, said compound of formula I

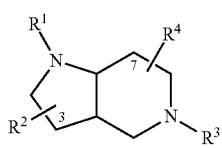

(I)

or a pharmaceutically acceptable salt thereof, wherein:

$R^1$ is arylalkyl or arylacyl, each of which is optionally substituted;

$R^2$ is hydrogen, alkyl, heteroalkyl, cycloalkyl, cycloheteroalkyl, aryl, or arylalkyl, each of which is optionally substituted;

$R^3$ is arylalkyl or arylacyl, each of which is optionally substituted; and $R^4$ is hydrogen, alkyl, heteroalkyl, cycloalkyl, cycloheteroalkyl, aryl, or arylalkyl, each of which is optionally substituted.

In another embodiment, described herein is a pharmaceutical composition comprising the compound of formula I above, or a pharmaceutically acceptable salt thereof.

In another embodiment, the stereochemistry of the ring fusion of the compound of formula I is syn. In another embodiment, the stereochemistry of the ring fusion of the compound of formula I is as follows:

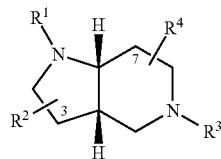

including pharmaceutically acceptable salts thereof. In another embodiment, the stereochemistry of the ring fusion of the compound of formula I is as follows:

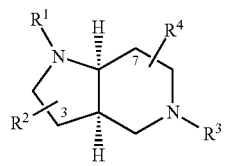

including pharmaceutically acceptable salts thereof. In another embodiment, the stereochemistry of the ring fusion and C-3 of the compound of formula I are as follows:

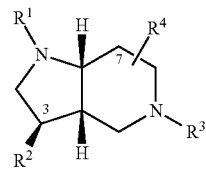

including pharmaceutically acceptable salts thereof. In another embodiment, the stereochemistry of the ring fusion of the compound of formula I is as follows:

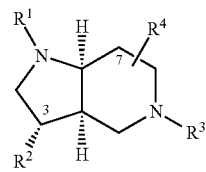

including pharmaceutically acceptable salts thereof.

In another embodiment, the substituents $R^1$, $R^2$, $R^3$, and $R^4$ of the compounds of formula I described herein, including all stereochemical variations of the compounds described herein, are each independently selected from the following hereinbelow. In another embodiment, the substituent $R^1$ of the compound of formula I described herein is optionally substituted arylacyl. In another embodiment, the substituent $R^1$ of the compound of formula I described herein is an optionally substituted arylcarbonyl. In another embodiment, the substituent $R^1$ of the compound of formula I described herein is an optionally substituted benzoyl. In another embodiment, the substituent $R^1$ of the compound of formula I described herein is benzoyl. In another embodiment, the substituent $R^1$ of the compound of formula I described herein is optionally substituted picolinoyl. In another embodiment, the substituent $R^1$ of the compound of formula I described herein is picolinoyl. In another embodiment, the substituent $R^2$ of the compound of formula I described herein is optionally substituted aryl. In another embodiment, the substituent $R^2$ of the compound of formula I described herein is optionally substituted phenyl. In another embodiment, the substituent $R^2$ of the compound of formula I described herein is phenyl substituted with halo, alkoxy, or a combination thereof. In another embodiment, the substituent $R^3$ of the compound of formula I described herein is optionally substituted arylalkyl. In another embodiment, the substituent $R^3$ of the compound of formula I described herein is optionally substituted arylmethylene. In another embodiment, the substituent $R^3$ of the compound of formula I described herein is optionally substituted benzyl. In another embodiment, the substituent $R^3$ of the compound of formula I described herein is benzyl substituted with an electron withdrawing group. In another embodiment, the substituent $R^3$ of the compound of formula I described herein is halo substituted benzyl. In another embodiment, the substituent $R^4$ of the compound of formula I described herein is hydrogen or alkyl. In another embodiment, the substituent $R^4$ of the compound of formula I described herein is hydrogen. In another embodiment, the substituent $R^2$ of the compound of formula I described herein is at C-3.

In another embodiment, described herein is the use of one or more of the compounds described herein in the manufacture of a medicament for treating a patient having a viral disease. Illustratively, the viral disease is hepatitis C.

In another embodiment, described herein is a method for treating a patient having a viral disease, illustratively hepatitis C, and the like, the method comprising the step of administering to the patient a therapeutically effective amount of one or more of the compounds described herein alone or as a composition with one or more carriers, diluents, or excipients, or a combination thereof.

It is to be understood that each of the foregoing selections for $R^1$, $R^2$, $R^3$, and $R^4$ are described herein for each of the stereochemical embodiments of formula I. It is to be further understood that each of the foregoing selections for $R^1$, $R^2$, $R^3$, and $R^4$ may be combined with each other in every possible combination, each of which forms a description of a further illustrative embodiment of the invention. For example, in one such combination, described herein are compounds of formula I, including any of the stereochemical embodiments of formula I, where $R^1$ is an optionally substituted arylacyl and $R^2$ is optionally substituted aryl. In another such combination, described herein are compounds of formula I, including any of the stereochemical embodiments of formula I, where $R^1$ is an optionally substituted benzoyl; $R^2$ is optionally substituted aryl; and $R^3$ is optionally substituted arylalkyl. In another such combination, described herein are compounds of formula I, including any of the stereochemical embodiments of formula I, where $R^1$ is benzoyl; $R^2$ is optionally substituted aryl; $R^3$ is benzyl substituted with an electron withdrawing group; and $R^4$ is hydrogen.

EXAMPLES

The following examples further illustrate specific embodiments of the invention; however, the following examples should not be interpreted in any way to limit the invention.

Example

Test Compounds

The substituted perhydropyrrolopyridines described herein are obtained from commercial suppliers (>90% purity) and used as is.

Method Example

Chimeric Mouse Model

The mouse model used herein is similar to those previously described in Kneteman et al., Hepatology, 2006, 43, 1346 and Kneteman et al., Hepatology, 2009, 49, 745. The animals used are homozygous albumin (Alb)-urokinase plasminogen activator (uPA)/severe combined immunodeficient (SCID) mice, and are housed in a virus-free/antigen-free environment until ready for use.

Method Example

Isolation and Transplantation of Human Hepatocytes

Segments of human liver tissue (~20 cm3) are flushed with cold phosphate-buffered saline and rapidly transported to the tissue isolation laboratory. Hepatocytes are isolated and purified using collagenase-based perfusion with 0.38 mg/ml Liberase CI solution (Boehringer Mannheim), using techniques described in Mercer et al., Hepatitis C virus replication in mice with chimeric human livers, Nat. Med. 2001, 7, 927-933. Recipient mice (5-14 days old uPA/SCID mice) are anesthetized with halothane/O2, and 1×106 viable hepatocytes are injected into the inferior pole of the spleen. The hepatocytes then transit on their own to the liver where they implant and expand.

Method Example

Human α-1 Antitrypsin Analysis

Human α-1 antitrypsin (hAAT) analysis is used to confirm stable ongoing function of the human hepatocyte grafts and to determine whether any change in HCV titer is attributable to hepatocyte death or injury. Mouse serum is analyzed by sandwich enzyme-linked immunosorbent assay as described in Kneteman et al., Hepatology, 2006, 43, 1346. Briefly, samples of mouse serum (2 ul) are diluted 1/100 in blocking buffer and analyzed by sandwich ELISA using a polyclonal goat anti-human alpha1-antitrypsin (hAAT) antibody (#81902, Diasorin, Stillwater Minn.) as the capturing antibody. A portion of the same antibody is cross-linked to horseradish peroxidase (#31489, Pierce, Rockford, Ill.) and used as the secondary antibody, with signal detection by 3,3',5,5'-tetramethylbenzidine (Sigma, St. Louis, Mo.).

Method Example

HCV Isolation and Quantitation

Murine serum analysis is performed in blinded fashion using the Cobas Amplicor HCV Monitor system (Roche Diagnostics). Lower limit of quantification is 600 IU/ml. Viral RNA is extracted using Buffer AVL from Qiagen (19073) according to the manufacturer's instructions. The RNA is transcribed to cDNA with a HCV specific primer (5'-AGGTTTAGGATTCGTGCTCAT (SEQ ID NO: 1)) with a High Capacity RNA to cDNA kit (Applied Biosystems, #4369016) according to the manufacturer's directions. RT-PCR is performed using an ABI 7300 Real Time PCR system and Taqman chemistry, with all measurements done in duplicate. 6-FAM-CACCCTATCAGGCAGTACCACAAGGCC-TAMRA (SEQ ID NO: 2) is used as the HCV specific detection probe and a primer set detecting the conserved 5'UTR region of HCV (5'-TGCGGAACCGGTGAGTACA (SEQ ID NO: 3), 5'-AGGTTTAGGATTCGTGCTCAT (SEQ ID NO: 4)). For absolute quantitation, a standard curve of known dilutions of a plasmid containing the sequence for HCV variant H77c (pCV-H77c) is created, alongside an Optiquant HCV RNA high control (Optiquant).

Method Example

Experimental Conduct

Six weeks after hepatocyte transplantation, mice are screened for serum hAAT, and animals above a 100-μg/mL cutoff are inoculated by intraperitioneal injection with 100 μg genotype 1a HCV-laden human serum (approximately 2×10$^5$ copies/mL). Baseline HCV levels are obtained at 1 and 2 weeks after inoculation, and mice with titers above 2×10$^4$ copies/mL are allocated to experimental groups. Allocation is sought to balance groups for HCV titers, hAAT levels, sex, and weight with decreasing priority.

Method Example

The following protocol is used for the evaluation of PK parameters and tolerance of the animals for the test compound. The protocol includes three escalating dose levels for each of the compounds administered at a volume of 5 mL/kg once a day by intra-peritoneal (IP) injection. The tolerance is determined over a fourteen day treatment course. The study animals include three 5-mouse groups. Also included is one 5-mouse control group injected with 5 mL/kg of a vehicle. The mouse groups include both male and female 3-month old mice, such as murine KMT Mice™, with a weight range of ≥12.0 g. Blood samples are drawn via the central tail artery of the animal for measurement of serum concentrations of the substituted perhydro pyrrolopyridines on the morning of Day 8. immediately prior to the compound dose (trough sample 24 hours post the Day 7 dose) and on the morning of Day 15 (trough sample 24 hours post the final Day 14 dose). A volume of approximately 100 μL is collected into tubes, allowed to clot at 2-8° C., centrifuged, and the serum removed from above the clot pellet and stored frozen at −80° C. until ready for concentration measurement.

Method Example

The following protocol is used for efficacy evaluation of the substituted perhydro pyrrolopyridines against HCV infection. The protocol includes three dose levels that are selected based on the tolerability and PK results from the study described herein. The efficacy of each substituted perhydro pyrrolopyridine is determined over a fourteen day treatment course and seven day follow-up period employing three escalating dose levels of drug administered at a volume of 5 mL/kg once a day by intraperitoneal injection. The baseline animal acceptance criteria are as follows: minimum hAAT value=80; minimum HCV value=$1 \times 10^4$ IU/mL; health status cutoff≤1-2. The study animals include three 5-mouse groups. Also included is one 5-mouse control group injected with 5 mL/kg of a vehicle. The mouse groups include both male and female 3-month old mice, such as murine KMT Mice™, with a weight range of ≥12.0 g. Blood samples are drawn via the central tail artery for measurement of baseline serum concentrations of hAAT and HCV on Day 3. Subsequent blood draws are made the morning of Day 7, immediately prior to compound dosing, the morning of Day 14, twenty-four hours after the final compound dose administered at approximately 0800 h the previous day and on Day 21, seven days after the last compound dose. A volume of approximately 100 μL is collected into tubes, allowed to clot at 2-8° C., centrifuged and the serum removed from above the clot pellet. Serum samples are stored frozen at −80° C. until ready for testing for HCV and hAAT levels.

Method Example

Assay for Anti-HCV Efficacy

In the past, HCV studies involved mainly infected patients and chimpanzees. Recently, a robust HCV infection system was developed with cells derived from the Huh-7 human hepatoma cell line (see, for example, Yu et al., "Development of a cell-based hepatitis C virus infection fluorescent resonance energy transfer assay for high-throughput antiviral compound screening" Antimicrob Agents Chemother. 2009 53:4311-4319 for additional details regarding growing virus stocks, maintenance of the Huh-7 cells, infection parameters, and HCV titers determinations; and Yu & Uprichard "Cell-based hepatitis C virus infection fluorescence resonance energy transfer (FRET) assay for antiviral compound screening" Curr Protoc Microbiol. 2010; Chapter 17: Unit 17.5). Briefly, the assay is based on the unique JFH-1 HCV consensus cDNA derived from an HCV patient. Using reverse genetics, the infectious virus can be rescued from this HCV clone. The recovered viable JFH virus can be passaged serially in Huh-7 cells. For this reason, this system is amenable for testing the activity of potential drugs for their anti-HCV efficacy. The antiviral activity of the compounds described herein is tested in this system.

Initially, $6 \times 10^3$ Huh7-1 cells are incubated overnight in each well of collagen-coated BioCoat 96-well plates (BD Biosciences, Bedford, Mass.) in 0.2 mL 10% Medium composed of Dulbecco's modified Eagle's medium supplemented with 10% fetal bovine serum. Subsequently, at 2 day intervals, the cultures are replenished with fresh 0.2 mL 10% Medium. Once the cultures become confluent, they are continually replenished at 2 day intervals with fresh 0.2 mL 10% Medium that also includes 1% dimethyl sulfoxide (DMSO). After 20 days of these replenishments, the Huh7-1 cultures are incubated with fresh 1% Medium (same as 10% Medium except that the serum level is 1%) containing HCV at a multiplicity of infection (MOI) of 0.05 focus forming units (ffu)/cell. The HCV (JFH-1wt Huh7) stock titer is $1.5 \times 10^5$ ffu/mL. The next day (day 1 post-infection) and 2 days later (day 3 post-infection) the media are replenished with fresh 1% Medium containing the test compounds dissolved in DMSO. On the 5th day of treatment with the compounds, cell lysates are collected for RNA isolation and Real Time-quantitative Reverse Transcription Polymerase Chain Reaction (RT-qPCR) and culture media are collected for cytotoxicity analysis.

Total RNA is isolated from cells by the guanidine thiocyanate method using standard protocols. One μg RNA is used for cDNA synthesis using TaqMan reverse transcription reagents (Applied Biosystems, Foster City, Calif.) followed by real-time PCR using an Applied Biosystems 7300 real-time thermocycler. Illustrative thermal cycling consists of initial denaturation of 10 min at 95° C. followed by 40 cycles of denaturation (15 s at 95° C.) and annealing/extension (1 m at 60° C.). HCV and human glyceraldehyde-3-phosphate dehydrogenase (GAPDH) RNA levels are determined relative to a standard curve of serial dilutions of plasmid containing JFH-1 HCV or GAPDH cDNA. The PCR primers used to detect GAPDH and HCV are illustratively: GAPDH (NMX002046) 5'-GAAGGTGAAGGTCGGAGTC-3' (SEQ ID NO: 5) (sense) and 5'-GAAGATGGTGATGGGATTTC-3' (SEQ ID NO: 6) (anti-sense) JFH-1 HCV (AB047639) 5'-TCTGCGGAACCGGTGAGTA-3' (SEQ ID NO: 7) (sense) and 5'-TCAGGCAGTACCACAAGGC-3' (SEQ ID NO: 8) (anti-sense).

Test compounds were also evaluated in a conventional cytotoxicity assay. In each case, the test compound did not exhibit cytotoxicity at 5 μM. It is appreciated that the lack of cyctoxicity supports the conclusion that the test compound activity in reducing viral titer is specific to the viral disease.

Figure 2:
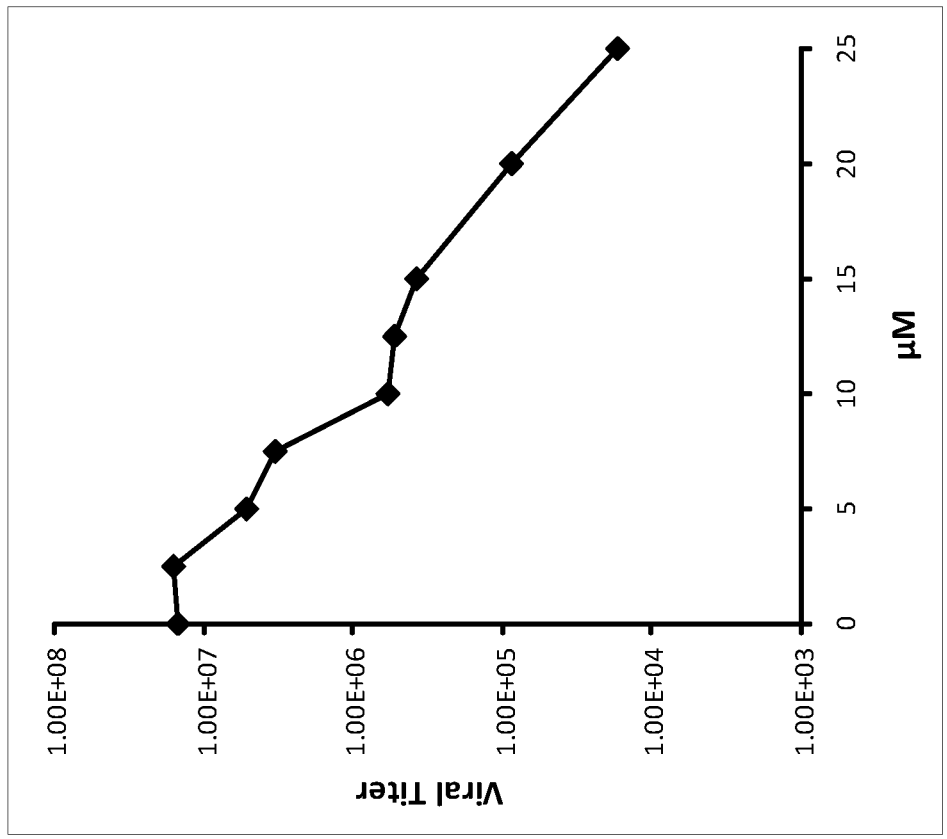
FIG. 2. Dose-response curve (μM) showing intracellular HCV RNA levels for cultures incubated with COMPOUND EXAMPLE 2: $Ar^1$=Ph, $Ar^2$=4-MeO—$C_6H_4$, $Ar^3$=4-F—$C_6H_4$.
Figure 4:
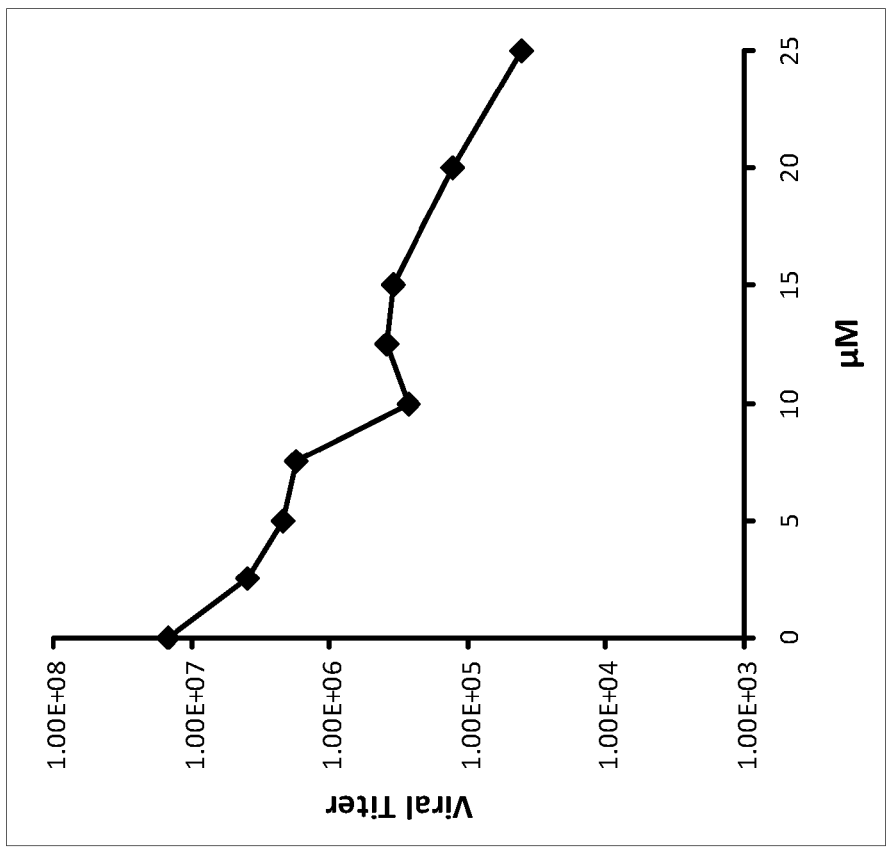
FIG. 4. Dose-response curve (μM) showing intracellular HCV RNA levels for cultures incubated with COMPOUND EXAMPLE 1: $Ar^1$=3-Pyridyl, $Ar^2$=4-F—$C_6H_4$, $Ar^3$=4-Cl—$C_6H_4$.
Figure 3:
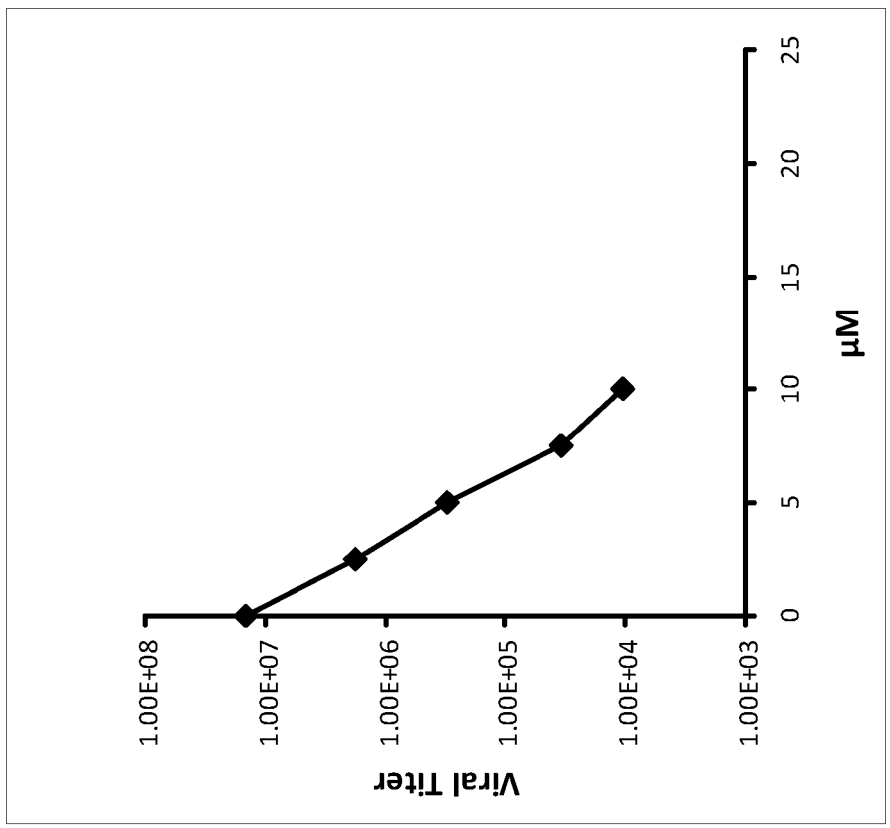
FIG. 3. Dose-response curve (μM) showing intracellular HCV RNA levels for cultures incubated with COMPOUND EXAMPLE 1: $Ar^1$=Ph, $Ar^2$=4-MeO—$C_6H_4$, $Ar^3$=3-F—$C_6H_4$.
Figure 6:
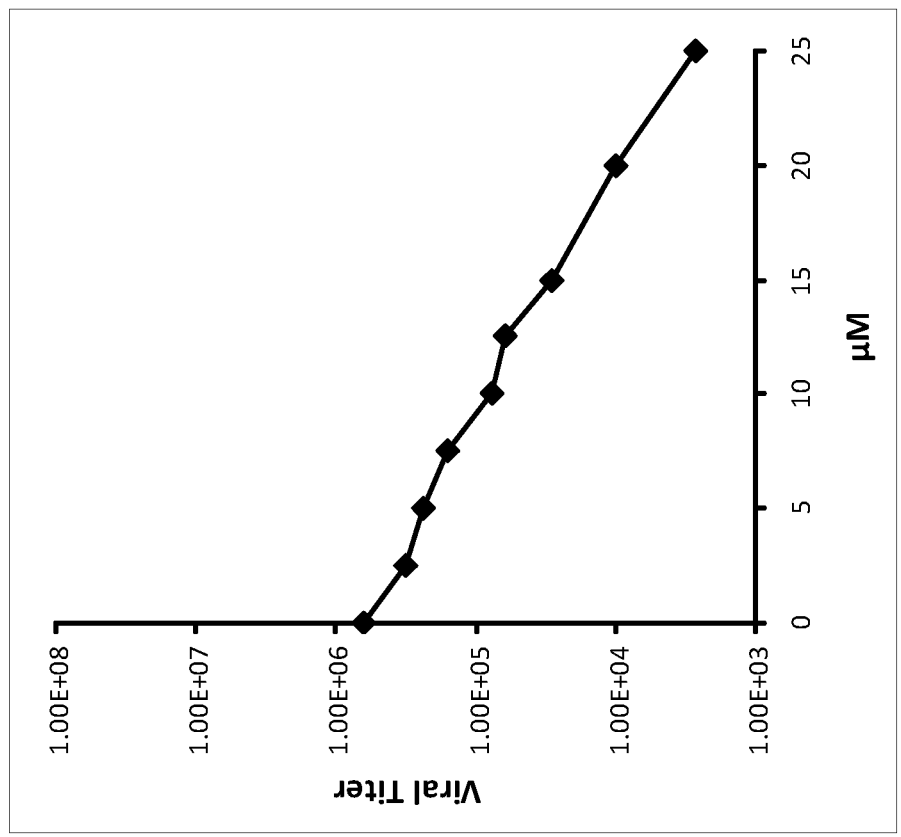
FIG. 6. Dose-response curve (μM) showing intracellular HCV RNA levels for cultures incubated with COMPOUND EXAMPLE 2: $Ar^1$=Ph, $Ar^2$=4-F—$C_6H_4$, $Ar^3$=3-F—$C_6H_4$.
Figure 5:
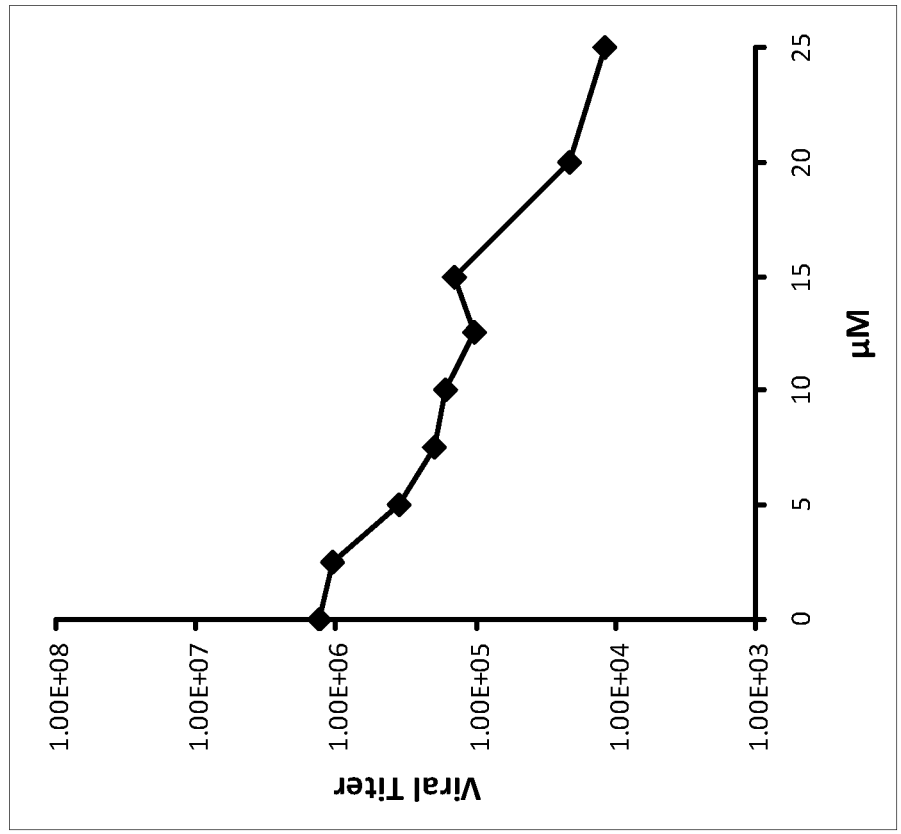
FIG. 5. Dose-response curve (μM) showing intracellular HCV RNA levels for cultures incubated with COMPOUND EXAMPLE 2: $Ar^1$=4-Pyridyl, $Ar^2$=4-F—$C_6H_4$, $Ar^3$=2-Cl—$C_6H_4$.
Figure 7:
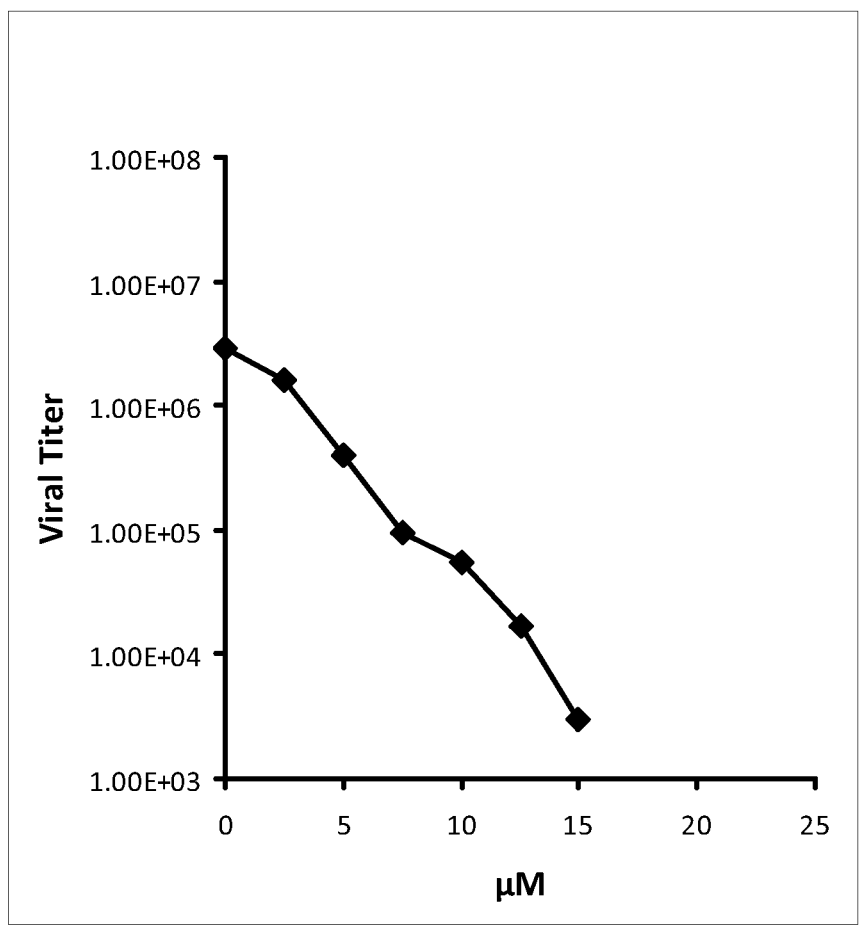
FIG. 7. Dose-response curve (μM) showing intracellular HCV RNA levels for cultures incubated with COMPOUND EXAMPLE 1: $Ar^1$=Ph, $Ar^2$=4-F—$C_6H_4$, $Ar^3$=4-F—$C_6H_4$.

FIGS. 1-7 illustrate the intracellular HCV RNA levels when cultures are incubated with the selected test compounds at the doses shown. When HCV RNA levels are compared among the samples, the data may indicate that the compounds cause a dose dependent decrease in HCV RNA levels relative to the mock-treated (no compound added) HCV infected control.

Compound Example 1

The following compounds are described herein:

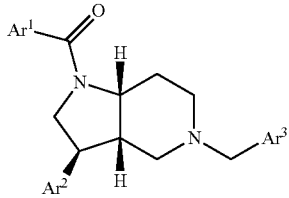

| Ar¹ | Ar² | Ar³ | Activity |
|---|---|---|---|
| Ph | 4-F—C$_6$H$_4$ | 4-F—C$_6$H$_4$ | +++ |
| 3-Pyridyl | 4-F—C$_6$H$_4$ | 4-Cl—C$_6$H$_4$ | +++ |
| Ph | 4-F—C$_6$H$_4$ | 3-MeO—C$_6$H$_4$ | +++ |
| Ph | 4-MeO—C$_6$H$_4$ | 3-F—C$_6$H$_4$ | +++ |
| 2-F—C$_6$H$_4$ | 3-Thienyl | 4-F—C$_6$H$_4$ | +++ |
| Ph | 4-F—C$_6$H$_4$ | 2-F—C$_6$H$_4$ | ++ |
| 2-Thienyl | 4-F—C$_6$H$_4$ | 4-F—C$_6$H$_4$ | ++ |
| Ph | 4-F—C$_6$H$_4$ | Ph | ++ |
| Ph | 4-F—C$_6$H$_4$ | 4-MeO—C$_6$H$_4$ | ++ |
| Ph | 4-MeO—C$_6$H$_4$ | 2-F—C$_6$H$_4$ | ++ |
| 2-F—C$_6$H$_4$ | 3-Thienyl | 3-Me—C$_6$H$_4$ | ++ |
| 2-F—C$_6$H$_4$ | 3-Thienyl | 3-F—C$_6$H$_4$ | ++ |
| Ph | 3-MeO—C$_6$H$_4$ | 3-Thienyl | ++ |
| 3-Pyridyl | 4-F—C$_6$H$_4$ | Ph | ++ |
| 2-Thienyl | 4-F—C$_6$H$_4$ | 2-F—C$_6$H$_4$ | + |
| 2-Thienyl | 4-F—C$_6$H$_4$ | 3-F—C$_6$H$_4$ | + |
| Ph | 3-MeO—C$_6$H$_4$ | 2-F—C$_6$H$_4$ | + |
| Ph | 3-MeO—C$_6$H$_4$ | 4-F—C$_6$H$_4$ | + |
| 2-F—C$_6$H$_4$ | 3-Thienyl | 3-Thienyl | + |
| Ph | 3-MeO—C$_6$H$_4$ | 2-Me—C$_6$H$_4$ | + |
| Ph | 3-MeO—C$_6$H$_4$ | 4-Me—C$_6$H$_4$ | + |
| 3-Pyridyl | 4-F—C$_6$H$_4$ | 3-Me—C$_6$H$_4$ | + |
| 2-Pyridyl | 4-F—C$_6$H$_4$ | 4-Cl—C$_6$H$_4$ | − |
| 3-Pyridyl | 4-F—C$_6$H$_4$ | 4-MeO—C$_6$H$_4$ | − |
| Ph | 4-MeO—C$_6$H$_4$ | Ph | − |
| 2-Pyridyl | 4-F—C$_6$H$_4$ | 4-MeO—C$_6$H$_4$ | − |
| 2-Pyridyl | 4-F—C$_6$H$_4$ | 3-MeO—C$_6$H$_4$ | − |
| Ph | 4-MeO—C$_6$H$_4$ | 2-Thienyl | − |
| 2-Pyridyl | 4-F—C$_6$H$_4$ | 2-F—C$_6$H$_4$ | − |
| Ph | 3-MeO—C$_6$H$_4$ | 3-F—C$_6$H$_4$ | − |
| Ph | 3-Thienyl | 2-Thienyl | − |
| Ph | 3-Thienyl | 3-Thienyl | − |
| 4-Pyridyl | 3-Thienyl | 2-Thienyl | − |
| 4-Pyridyl | 3-Thienyl | 3-Thienyl | − |
| 2-F—C$_6$H$_4$ | 3-Thienyl | Ph | − |
| 2-F—C$_6$H$_4$ | 3-Thienyl | 2-F—C$_6$H$_4$ | − |
| 2-F—C$_6$H$_4$ | 3-Thienyl | 2-Thienyl | − |
| 2-F—C$_6$H$_4$ | 3-Thienyl | 4-Me—C$_6$H$_4$ | − |
| 2-F—C$_6$H$_4$ | 3-Thienyl | 4-Pyridyl | − |
| 2-F—C$_6$H$_4$ | 3-Thienyl | 3-Pyridyl | − |
| 2-F—C$_6$H$_4$ | 3-Thienyl | 2-Pyridyl | − |
| 4-F—C$_6$H$_4$ | 3-Thienyl | 2-Thienyl | − |
| Ph | 3-MeO—C$_6$H$_4$ | Ph | − |
| Ph | 3-MeO—C$_6$H$_4$ | 2-Thienyl | − |
| Ph | 3-MeO—C$_6$H$_4$ | 4-Pyridyl | − |
| Ph | 3-MeO—C$_6$H$_4$ | 3-Pyridyl | − |
| Ph | 3-MeO—C$_6$H$_4$ | 2-Pyridyl | − |
| 3-Pyridyl | 4-F—C$_6$H$_4$ | 2-Me—C$_6$H$_4$ | − |
| 3-Pyridyl | 4-F—C$_6$H$_4$ | 3-Pyridyl | − |
| 2-Pyridyl | 4-F—C$_6$H$_4$ | Ph | − |
| 2-Pyridyl | 4-F—C$_6$H$_4$ | 3-Pyridyl | − |
| 2-Pyridyl | 4-F—C$_6$H$_4$ | 2-Pyridyl | − |
| 2-Pyridyl | 4-F—C$_6$H$_4$ | 3-Me—C$_6$H$_4$ | − |
| 2-Thienyl | 4-F—C$_6$H$_4$ | Ph | − |
| 2-Thienyl | 4-F—C$_6$H$_4$ | 3-Pyridyl | − |
| 2-Thienyl | 4-F—C$_6$H$_4$ | 2-Pyridyl | − |
| 2-Thienyl | 4-F—C$_6$H$_4$ | 2-Me—C$_6$H$_4$ | − |
| Ph | 4-MeO—C$_6$H$_4$ | 2-Pyridyl | − |
| Ph | 4-MeO—C$_6$H$_4$ | 3-Thienyl | − |
| 3-Pyridyl | 4-F—C$_6$H$_4$ | 2-F—C$_6$H$_4$ | − |
| 3-Pyridyl | 4-F—C$_6$H$_4$ | 4-F—C$_6$H$_4$ | − |
| 3-Pyridyl | 4-F—C$_6$H$_4$ | 2-Cl—C$_6$H$_4$ | − |
| 3-Pyridyl | 4-F—C$_6$H$_4$ | 2-Thienyl | − |
| 3-Pyridyl | 4-F—C$_6$H$_4$ | 4-Pyridyl | − |

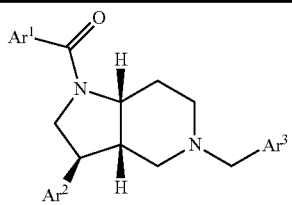

| Ar¹ | Ar² | Ar³ | Activity |
|---|---|---|---|
| 3-Pyridyl | 4-F—C$_6$H$_4$ | 3-Thienyl | − |
| 4-Pyridyl | 4-F—C$_6$H$_4$ | 4-MeO—C$_6$H$_4$ | − |
| 4-Pyridyl | 4-F—C$_6$H$_4$ | 2-Thienyl | − |
| 4-Pyridyl | 4-F—C$_6$H$_4$ | 3-Thienyl | − |

"+++" = ≤30% viral titer at 5 μM
"++" = ≤60% viral titer at 5 μM
"+" = ≤60% viral titer at 15 μM
"−" = >60% viral titer at 15 μM (highest concentration tested)

Compound Example 2

The following compounds are described herein:

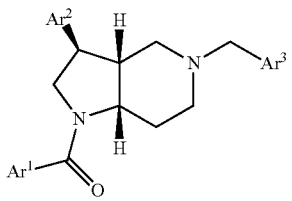

| Ar¹ | Ar² | Ar³ | Activity |
|---|---|---|---|
| Ph | 4-MeO—C$_6$H$_4$ | 4-F—C$_6$H$_4$ | +++ |
| 4-Pyridyl | 4-F—C$_6$H$_4$ | 2-Cl—C$_6$H$_4$ | +++ |
| Ph | 3-Thienyl | 2-F—C$_6$H$_4$ | +++ |
| Ph | 4-F—C$_6$H$_4$ | 3-F—C$_6$H$_4$ | ++ |
| Ph | 3-Thienyl | Ph | ++ |
| Ph | 3-Thienyl | 4-F—C$_6$H$_4$ | ++ |
| Ph | 3-Thienyl | 4-Cl—C$_6$H$_4$ | ++ |
| Ph | 3-Thienyl | 3,4-F$_2$—C$_6$H$_3$ | ++ |
| 3-Pyridyl | 4-F—C$_6$H$_4$ | 2-MeO—C$_6$H$_4$ | ++ |
| 4-Pyridyl | 4-F—C$_6$H$_4$ | 3-Me—C$_6$H$_4$ | ++ |
| Ph | 4-F—C$_6$H$_4$ | 1-Me-pyrazol-4-yl | + |
| Ph | 4-F—C$_6$H$_4$ | 1,5-Me$_2$-pyrazol-4-yl | + |
| Ph | 4-F—C$_6$H$_4$ | 1,3-Me$_2$-pyrazol-4-yl | + |
| Ph | 3-Thienyl | 4-MeO—C$_6$H$_4$ | + |
| 4-Pyridyl | 3-Thienyl | 4-F—C$_6$H$_4$ | + |
| 4-Pyridyl | 3-Thienyl | 4-Cl—C$_6$H$_4$ | + |
| 4-Pyridyl | 3-Thienyl | 3-Cl—C$_6$H$_4$ | + |
| 4-Pyridyl | 3-Thienyl | 3,4-F$_2$—C$_6$H$_3$ | + |
| 4-F—C$_6$H$_4$ | 3-Thienyl | Ph | + |
| 4-F—C$_6$H$_4$ | 3-Thienyl | 4-F—C$_6$H$_4$ | + |
| 3-Pyridyl | 4-F—C$_6$H$_4$ | 3-MeO—C$_6$H$_4$ | + |
| 4-Pyridyl | 4-F—C$_6$H$_4$ | 2-MeO—C$_6$H$_4$ | + |
| 2-Pyridyl | 4-F—C$_6$H$_4$ | 2-Cl—C$_6$H$_4$ | − |
| 4-Pyridyl | 4-F—C$_6$H$_4$ | 4-F—C$_6$H$_4$ | − |
| 2-Pyridyl | 4-F—C$_6$H$_4$ | 4-F—C$_6$H$_4$ | − |
| 2-Pyridyl | 4-F—C$_6$H$_4$ | 3-F—C$_6$H$_4$ | − |
| Ph | 3-Thienyl | 2-Cl—C$_6$H$_4$ | − |
| Ph | 3-Thienyl | 3-Pyridyl | − |
| Ph | 3-Thienyl | 3-MeO—C$_6$H$_4$ | − |
| Ph | 3-Thienyl | 2-MeO—C$_6$H$_4$ | − |
| Ph | 3-Thienyl | 3-Cl—C$_6$H$_4$ | − |
| Ph | 3-Thienyl | 2-Me—C$_6$H$_4$ | − |
| Ph | 3-Thienyl | 3-Me—C$_6$H$_4$ | − |
| Ph | 3-Thienyl | 3-F—C$_6$H$_4$ | − |
| Ph | 3-Thienyl | 2,3-F$_2$—C$_6$H$_4$ | − |
| 4-Pyridyl | 3-Thienyl | Ph | − |
| 4-Pyridyl | 3-Thienyl | 2-F—C$_6$H$_4$ | − |
| 4-Pyridyl | 3-Thienyl | 2-Cl—C$_6$H$_4$ | − |

-continued

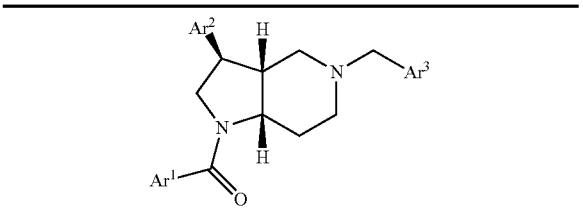

| Ar¹ | Ar² | Ar³ | Activity |
|---|---|---|---|
| 4-Pyridyl | 3-Thienyl | 4-MeO—$C_6H_4$ | − |
| 4-Pyridyl | 3-Thienyl | 4-Me—$C_6H_4$ | − |
| 4-Pyridyl | 3-Thienyl | 4-i-Pr—$C_6H_4$ | − |
| 4-Pyridyl | 3-Thienyl | 3-MeO—$C_6H_4$ | − |
| 4-Pyridyl | 3-Thienyl | 2-MeO—$C_6H_4$ | − |
| 4-Pyridyl | 3-Thienyl | 2-Me—$C_6H_4$ | − |
| 4-Pyridyl | 3-Thienyl | 2,3-$F_2$—$C_6H_4$ | − |
| 4-F—$C_6H_4$ | 3-Thienyl | 2-F—$C_6H_4$ | − |
| 4-F—$C_6H_4$ | 3-Thienyl | 4-Me—$C_6H_4$ | − |
| 4-F—$C_6H_4$ | 3-Thienyl | 4-Pyridyl | − |
| 4-F—$C_6H_4$ | 3-Thienyl | 3-Pyridyl | − |
| 4-F—$C_6H_4$ | 3-Thienyl | 2-Pyridyl | − |
| 4-F—$C_6H_4$ | 3-Thienyl | 2-Me—$C_6H_4$ | − |
| 4-F—$C_6H_4$ | 3-Thienyl | 3-Me—$C_6H_4$ | − |
| 4-F—$C_6H_4$ | 3-Thienyl | 3-F—$C_6H_4$ | − |
| 2-Pyridyl | 4-F—$C_6H_4$ | 2-Me—$C_6H_4$ | − |
| 3-Pyridyl | 4-F—$C_6H_4$ | 3-Pyridyl | − |
| 3-Pyridyl | 4-F—$C_6H_4$ | 2-Pyridyl | − |
| 3-Pyridyl | 4-F—$C_6H_4$ | 3-F—$C_6H_4$ | − |
| 3-Pyridyl | 4-F—$C_6H_4$ | 1,5-$Me_2$-pyrazol-4-yl | − |
| 3-Pyridyl | 4-F—$C_6H_4$ | 1,3-$Me_2$-pyrazol-4-yl | − |
| 4-Pyridyl | 4-F—$C_6H_4$ | Ph | − |
| 4-Pyridyl | 4-F—$C_6H_4$ | 2-F—$C_6H_4$ | − |
| 4-Pyridyl | 4-F—$C_6H_4$ | 4-Pyridyl | − |
| 4-Pyridyl | 4-F—$C_6H_4$ | 3-MeO—$C_6H_4$ | − |
| 4-Pyridyl | 4-F—$C_6H_4$ | 2-Pyridyl | − |
| 4-Pyridyl | 4-F—$C_6H_4$ | 2-Me—$C_6H_4$ | − |
| 4-Pyridyl | 4-F—$C_6H_4$ | 3-F—$C_6H_4$ | − |

"+++" = ≤30% viral titer at 5 μM
"++" = ≤60% viral titer at 5 μM
"+" = ≤60% viral titer at 15 μM
"−" = >60% viral titer at 15 μM (highest concentration tested)

What is claimed is:

1. A method for treating a patient having hepatitis C, the method comprising the step of administering to the patient a therapeutically effective amount of one or more compounds of the formula

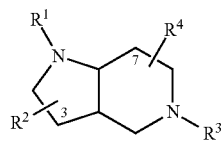

or a pharmaceutically acceptable salt thereof, wherein:
$R^1$ is arylalkyl or arylacyl, each of which is optionally substituted;
$R^2$ is hydrogen, alkyl, heteroalkyl, cycloalkyl, cycloheteroalkyl, aryl, or arylalkyl, each of which is optionally substituted;
$R^3$ is arylalkyl or arylacyl, each of which is optionally substituted; and
$R^4$ is hydrogen, alkyl, heteroalkyl, cycloalkyl, cycloheteroalkyl, aryl, or arylalkyl, each of which is optionally substituted,
alone or as a composition with one or more carriers, diluents, or excipients, or a combination thereof.

2. The method of claim 1 wherein the stereochemistry of the ring fusion in the compound is syn.

3. The method of claim 1 wherein the compound is of the formula

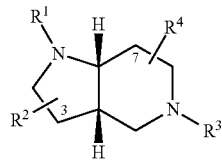

or a pharmaceutically acceptable salt thereof.

4. The method of claim 1 wherein the compound is of the formula

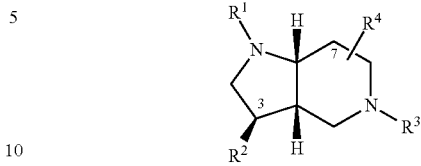

or a pharmaceutically acceptable salt thereof.

5. The method of claim 1 wherein $R^1$ is optionally substituted arylacyl.

6. The method of claim 1 wherein $R^1$ is optionally substituted arylcarbonyl.

7. The method of claim 1 wherein $R^1$ is optionally substituted benzoyl.

8. The method of claim 1 wherein $R^1$ is benzoyl.

9. The method of claim 1 wherein $R^1$ is optionally substituted picolinoyl.

10. The method of claim 1 wherein $R^1$ is picolinoyl.

11. The method of claim 1 wherein $R^2$ is optionally substituted aryl.

12. The method of claim 1 wherein $R^2$ is optionally substituted phenyl.

13. The method of claim 1 wherein $R^2$ is phenyl substituted with halo, alkoxy, or a combination thereof.

14. The method of claim 1 wherein $R^3$ is optionally substituted arylalkyl.

15. The method of claim 1 wherein $R^3$ is optionally substituted arylmethylene.

16. The method of claim 1 wherein $R^3$ is optionally substituted benzyl.

17. The method of claim 1 wherein $R^3$ is benzyl substituted with an electron withdrawing group.

18. The method of claim 1 wherein $R^3$ is halo substituted benzyl.

19. The method of claim 1 wherein R4 is hydrogen or alkyl.

20. The method of claim 1 wherein $R^4$ is hydrogen.

* * * * *

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aggtttagga ttcgtgctca t                                                 21

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-6-FAM
<220> FEATURE:
<223> OTHER INFORMATION: 3'-TAMRA

<400> SEQUENCE: 2
caccctatca ggcagtacca caaggcc                                           27

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgcggaaccg gtgagtaca                                                    19
```

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
aggtttagga ttcgtgctca t                                             21

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
gaaggtgaag gtcggagtc                                                19

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
gaagatggtg atgggatttc                                               20

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
tctgcggaac cggtgagta                                                19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
tcaggcagta ccacaaggc                                                19